US00PP09768P

United States Patent [19]

Shiigi

[11] Patent Number: Plant 9,768

[45] Date of Patent: Dec. 24, 1996

[54] GUZMANIA 'PUNA GOLD'

[76] Inventor: David R. Shiigi, 35 Pau O Palae St., Hilo, Hi. 96720

[21] Appl. No.: 510,136

[22] Filed: Jul. 20, 1995

[51] Int. Cl.[6] ..... A01H 5/00

[52] U.S. Cl. ..... Plt./88.8

[58] Field of Search ..... Plt./88.8

*Primary Examiner*—James R. Feyrer

*Attorney, Agent, or Firm*—Daniel M. Chambers

[57] ABSTRACT

The plant of the disclosure is a new and novel interspecific Guzmania plant, named 'Puna Gold', which is characterized as a perennial monocot of medium size which is vigorous; and, upright, spreading in habit. Flowering is conspicuously yellow and very long lasting with color retention of between about 3 to 6 months. Extension of inflorescence is about 43 to 48 cm. over a plant of about 72 to 82 cm in width. The plant produces between 36 to 40 leaves for optimum plant size and balance with inflorescence. Bracts and flower parts are brilliant and pale yellow, respectively, with flowers in tight groupings of 263 to 273 individual flowers.

1 Drawing Sheet

BACKGROUND OF THE INVENTION

The present invention relates to a new and distinct cultivar of the genus Guzmania of the family Bromeliacea. Guzmanias are highly attractive plants and most known for their striking inflorescence. This new cultivar was the result of crossing *Guzmania memoria* (*G. lingulata* variety minor crossed with *G. lingulata* variety major) pollen plant and *Guzmania insignis* (*G. lingulata* variety splendens crossed with *G. zahnii*) seed parent in 1982.

I established approximately twenty plants out of a group of fifty seedlings raised in my shade house in the town of Pahoa in Puna District on the island of Hawaii. The plants were grown in 73% to 80% shade at 78° to 90° F. in the summer and 68° to 80° in the winter. The plants are medium size and more compact than *G. insignis* and the inflorescence includes the flower. The flower bracts and scape attain shades of red and yellow striations. The hybrid cultivar was discovered in 1986 as an offshoot of one of these fifty plants. The offshoot was entirely green without the red striations in the leaves characteristic of the parent and first bloomed in 1987. The plant took from 18 to 20 months to bloom. The entire star shaped flower was composed of different shades of yellow distinct from the reddish outer bracts and yellow center of the parent. This plant produced nine offsets in greenhouses owned by the applicant. The distinction of a new cultivar was recognized by the striking yellow color of the inflorescence which is significantly different from other known Guzmania hybrids.

The pollen plant, *G. memoria,* is a hybrid of *G. lingulata* variety minor and *G. lingulata* variety major. *G. memoria* is of medium size and ranges from 60 to 68 centimeters (cm) in diameter producing 30 to 35 leaves. The plant rises to a height of 20 to 28 cm without inflorescence. When in bloom the inflorescence rises from the center of the plant to a height of 28 to 34 cm, the plant having an overall height of 32 to 42 cm. The basal leaves range in length from 38 to 42 cm. The leaves are 5 to 6 cm wide beginning at the base and extending 8 to 10 cm from the base tapering to a width of 3 to 3.5 cm for a majority of the remainder of its length terminating in a tip 2 cm wide and 3 cm long. There are approximately 13 to 16 bracts which form 14 to 19 cm diameter star when viewed from the top of the plant. Each bract ranges in length from 2 to 2.5 cm having a width of 4 to 5 cm at its widest point tapering to 2.5 to 3 cm at midpoint terminating in a tip 2 to 2.5 cm in width. The bracts are red-orange in color and the inner floral cone is yellow with white tips.

The seed plant, *G. insignis,* is a hybrid of *G. lingulata* variety Splendens and *G. zahnii. G. insignis* is a medium to large size plant having a diameter ranging from 83 to 88 cm with a height ranging from 82 to 87 cm. The basal leaves range from 50 to 56 cm in length having a width ranging from 6 to 7 cm from the base extending from the base approximately 14 to 16 cm tapering to 2 to 3.5 cm for a majority of the remainder of its length terminating in a tip 2 cm in width. The leaves have fine red stripes emanating from the base approximately 15 to 17 cm along the length of the leaves. The bract cluster contains approximately 16 to 20 bracts which range from 15 to 10 cm in diameter forming a star shape when viewed from above. The bracts are red with fine stripes ranging from red to yellow in color. The inner floral cone is yellow.

DESCRIPTIONS OF THE DRAWINGS

DETAILED DESCRIPTION OF THE INVENTION

Figure 1:
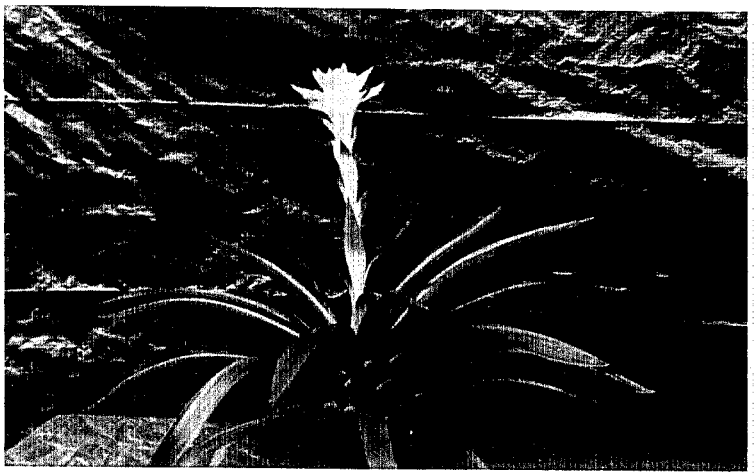
FIG. 1 is a photograph of a typical plant offshoot cut at 6 weeks which took 14 to 16 months to bloom of the present invention Guzmania "Puna Gold".
Figure 2:
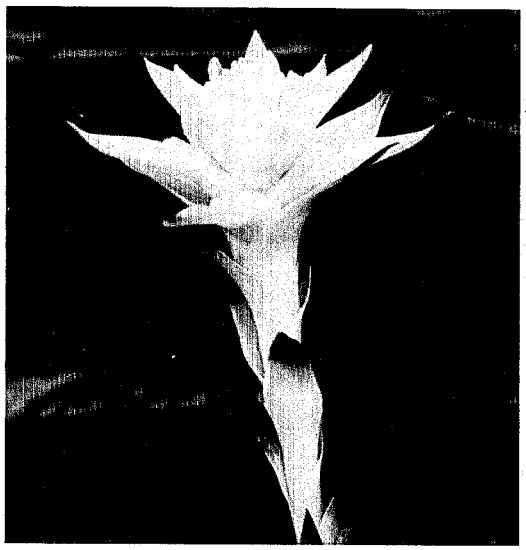
FIG. 2 is a close up photograph of the fully developed inflorescence and the yellow color characteristic of Guzmania "Puna Gold".
Figure 3:
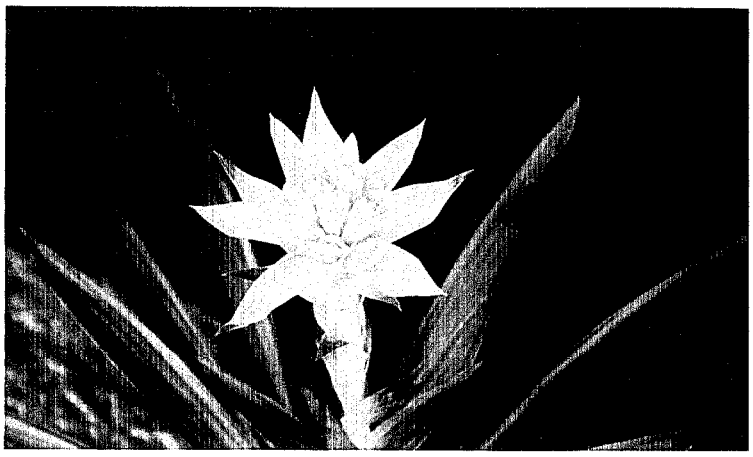
FIG. 3 is a top view photograph of the inflorescence showing the star shaped bracts and the darker inner floral bracts.

Certain details of the plant are set forth in the following descriptive notations. References to color are made to The Royal Horticultural Society Colour Chart.

PLANT

The name under which the disclosed plant will be known in commerce Guzmania "Puna Gold". Guzmania "Puna Gold" was created by crossing the seed parent, *G. insignis* (*G. lingulata* variety splendens crossed with *G. zahnii*) with the pollen parent — *G. memoria* (*G. lingulata* variety minor crossed with *G. lingulata* variety major). The instant hybrid is monocot and perennial. The plant is of medium size, vigorous, upright, spreading, open, vase formed, and tender. The diameter of a fully grown Guzmania "Puna Gold" is approximately 78 to 82 cm. The height of the plant including the flower bracts and flowers is approximately 54 to 59 cm and the height of the foliage is approximately 48 to 52 cm.

LEAVES

The leaves are light to medium green (Royal Historical Society color 137-A, "RHS137-A") on the adaxial side and medium green (RHS137-C) on the abaxial side. They are linear and smooth. The length of the basal leaves are approximately 43 to 46 cm. The leaves have a width of 6 to 5 cm at the base of the rosette for a length of 8 cm, becoming 4.5 to 4.0 for a length of 2 cm, then tapering to 3.5 to 3.0 cm for a length of 8 cm, becoming 2.5 cm for a length of 18 cm, then tapering to 2.0 cm for a length of 5.5 cm, becoming 1.5 to 1.0 cm for a length of 4 cm and finally tapering to 0.5 cm for a length of 1 cm to the apex. Each emerging leaf is gradually shorter than the last. The plant produces approximately 36 to 40 leaves.

BRACTS

The bracts are star shaped symmetrical points (when viewed from above) which can extend from the center of the mature plant approximately 43 to 48 cm. Approximately 18 individual bracts form the main inflorescence. The bracts are 8 to 9 cm in length and approximately 3.5 cm wide at the base gradually tapering to an apex approximately a 0.5 cm in width. The predominant color of the main inflorescence is yellow (RHS8-A). The apex of the lower main bracts are green (RHS144-A). There are approximately 12 to 14 cone shaped main inner floral bracts which range in length from 2.5 to 3 cm and range in width from about 2 to 4 cm. The color of these bracts is bright yellow (RHS17-B). The basal bracts are yellow-green to light green (RHS8-C to RHS144-A) ranging in length from 20 to 22 cm in the lower bracts to 9 to 12 cm in the upper bracts. The inflorescence will retain its color for approximately 3 to 6 months.

FLOWER

The flower is a pale yellow (RHS8-C) cylindrical corolla 1.5 cm at its anthesis. The mid-range of the flower is not visible without dissection. The flower color is pale yellow (RHS8-C) and comprises three sepals 0.5 cm wide and 3 cm in length. The flowers have three petals of a pale yellow color, (RHS8-C) ranging from 2 to 3 mm in width and 1 cm in length. Each flower has five to six stamens ranging in length from 1 to 1.5 cm in length and one stigma 1.5 cm in length. The flowers form a tight grouping of 263 to 273 individual flowers.

I claim:

1. A new and distinct hybrid cultivar named Guzmania "Puna Gold" obtained by crossing *Guzmania memoria* (*G. lingulata* variety minor crossed with *G. lingulata* variety major) and *Guzmania insignis* (*G. lingulata* variety splendens with *G. zahnii*) substantially as illustrated and described herein.

* * * * *